United States Patent [19]

Kummer et al.

[11] 4,169,956

[45] Oct. 2, 1979

[54] MANUFACTURE OF BUTANEDICARBOXYLIC ACID ESTERS

[75] Inventors: Rudolf Kummer, Frankenthal; Heinz-Walter Schneider, Ludwigshafen; Franz-Josef Weiss, Weinheim, all of Fed. Rep. of Germany

[73] Assignee: BASF Aktiengesellschaft, Fed. Rep. of Germany

[21] Appl. No.: 940,463

[22] Filed: Sep. 8, 1978

[30] Foreign Application Priority Data

Sep. 15, 1977 [DE] Fed. Rep. of Germany ....... 2741511

[51] Int. Cl.$^2$ .............................................. C07C 67/38
[52] U.S. Cl. .................................. 560/204; 560/206
[58] Field of Search ............................... 560/204, 206

[56] References Cited

U.S. PATENT DOCUMENTS

| | | | |
|---|---|---|---|
| 2,542,767 | 2/1951 | Gresham et al. ...................... | 560/204 |
| 3,507,891 | 4/1970 | Hearne et al. ........................ | 560/233 |
| 3,778,466 | 12/1973 | Matsuda ................................ | 560/206 |
| 3,856,832 | 12/1974 | Ethyl Corporation .............. | 560/204 |
| 4,041,057 | 8/1977 | Fanning ................................ | 560/204 |

OTHER PUBLICATIONS

Matsuda, Bull. Chem. Soc. Japan, 46, pp. 524–530, (1973).

*Primary Examiner*—Jane S. Myers
*Attorney, Agent, or Firm*—Keil & Witherspoon

[57] ABSTRACT

A process for the manufacture of butanedicarboxylic acid esters, wherein
(a) an aqueous cobalt salt solution is treated with carbon monoxide and hydrogen in the presence of active charcoal,
(b) the resulting aqueous solution is extracted with butadiene or with a hydrocarbon mixture containing butadiene,
(c) the butadiene, or butadiene/hydrocarbon mixture, containing cobalt carbonyl hydride, cobalt carbonyl and butenyl-cobalt tricarbonyl, is reacted with carbon monoxide and an excess of an alkanol of 1 to 4 carbon atoms in the presence of a tertiary nitrogen base,
(d) the tertiary nitrogen bases contained in the resulting reaction mixture are removed from the latter to the extent of leaving from 0.1 to 0.3 mole per mole of pentenoic acid ester, excess hydrocarbons are also removed, the pentenoic acid ester remaining in the reaction mixture is reacted with carbon monoxide and an alkanol of 1 to 4 carbon atoms, and thereafter excess alkanol and free nitrogen base are distilled off and
(e) the residual reaction mixture, containing cobalt catalysts, butanedicarboxylic acids and by-products is treated with an oxidizing agent in an aqueous acid medium and the mixture is separated into an organic phase, from which butanedicarboxylic acid esters are isolated by distillation, and an aqueous phase containing cobalt salts, which phase is extracted with a water-immiscible solvent.

3 Claims, No Drawings

MANUFACTURE OF BUTANEDICARBOXYLIC ACID ESTERS

The present invention relates to a process for the manufacture of butanedicarboxylic acid esters, in which butadiene or a hydrocarbon mixture containing butadiene is reacted with carbon monoxide and a lower alkanol in the presence of a tertiary nitrogen base and cobalt carbonyl at from 80° to 150° C. under superatmospheric pressure, and the pentenoic acid ester obtained is further reacted with carbon monoxide and a lower alkanol at from 140 to 200° C., under superatmospheric pressure, to give a butanedicarboxylic acid ester.

Bull. Chem. Soc. Japan 46 (1973), 524 et seq., discloses a two-stage process for the manufacture of adipic acid esters from butadiene, wherein butadiene is first reacted with carbon monoxide and an alkanol in the presence of cobalt carbonyl and a nitrogen base, e.g., pyridine or isoquinoline and, without removing the catalyst, the pentenoic acid ester formed is further reacted, in a subsequent stage, with carbon monoxide and an alkanol to give an adipic acid ester. However, in carrying out this process industrially it is necessary to recover and recycle the catalyst. For example, in the process disclosed in U.S. Pat. No. 3,778,466, the residue containing the catalyst is reused for the carbonylation after having distilled off the useful products. However, it has been found that the activity of the catalyst decreases substantially after, for example, four-fold use. This is attributable to the fact that on the one hand the catalyst is damaged during the distillation process, since cobalt carbonyl complexes are not heat-stable, whilst on the other hand the carbonylation results in by-products which affect the carbonylation and must therefore be removed continuously. Attempts have also already been made to separate the useful products from the catalyst-containing residue by extraction after the carbonylation reaction. For example, German Laid-Open Application DOS No. 2,159,139 discloses a process in which the methanol-containing carbonylation mixture is extracted with a hydrocarbon. It is true that this makes it possible to isolate the useful products without damaging the catalyst, and to recycle the methanolic catalyst-containing solution to the carbonylation reaction. However, this extractive separation is not a suitable method of removing by-products, e.g., polymeric butadienes, which are formed during the carbonylation. Hence, such products continuously accumulate on repeated reuse of the catalyst solution, and interfere with the carbonylation.

It is an object of the present invention to modify the carbonylation of butadiene, to give butanedicarboxylic acid esters, so that the catalyst metal is almost completely recovered in a form reusable for the carbonylation reaction, and at the same time harmful by-products are removed.

We have found that this object is achieved in a process for the manufacture of butanedicarboxylic acid esters, by reacting butadiene or a hydrocarbon mixture containing butadiene with carbon monoxide and an alkanol of 1 to 4 carbon atoms in the presence of a tertiary nitrogen base and a cobalt carbonyl compound at from 80° to 150° C. under superatmospheric pressure and then, without removing the cobalt catalyst, reacting the pentenoic acid ester obtained further with carbon monoxide and an alkanol of 1 to 4 carbon atoms at from 140° to 200° C. under superatmospheric pressure, to give a butanedicarboxylic acid ester, wherein (a) an aqueous cobalt salt solution is treated, at from 50 to 200° C., under pressures of from 50 to 500 bar, with excess carbon monoxide and hydrogen in the presence of active charcoal charged with cobalt carbonyl, (b) the resulting aqueous solution of cobalt carbonyl hydride is extracted with butadiene or a hydrocarbon mixture containing butadiene and the aqueous phase is separated off, (c) the butadiene, or butadiene-containing hydrocarbon mixture, which contains cobalt carbonyl hydride, cobalt carbonyl and butenyl-cobalt tricarbonyl is reacted with carbon monoxide and an excess of an alkanol of 1 to 4 carbon atoms in the presence of from 0.5 to 2 moles, per mole of butadiene, of a tertiary nitrogen base having a $pK_a$ of from 3 to 11, at from 80° to 150° C., under a pressure of from 300 to 2,000 bar, (d) the tertiary nitrogen bases contained in the reaction mixture thus obtained are removed to the extent of leaving from 0.1 to 0.3 mole per mole of pentenoic acid ester produced, excess hydrocarbon is also removed, the pentenoic acid ester remaining in the reaction mixture is reacted with carbon monoxide and an excess of an alkanol of 1 to 4 carbon atoms at from 140° to 200° C. under a pressure of from 100 to 400 bar in the presence of the amount of cobalt carbonyl and tertiary nitrogen base remaining in the reaction mixture and thereafter the excess alkanol and free tertiary nitrogen base are distilled off, and (e) the residual reaction mixture, containing catalyst, butanedicarboxylic acid ester and by-products, is treated with an oxidizing agent in an aqueous acid medium and the mixture is separated into an organic phase, from which butanedicarboxylic acid esters are isolated by distillation, and an aqueous phase containing cobalt salts, with the proviso that the aqueous phase containing cobalt salts is extracted with a water-immiscible solvent.

The novel process has the advantage that additional amounts of useful products are isolated from the aqueous phase. In addition, the process claimed has the advantage that no troublesome products are recycled with the aqueous phase. The $C_5$- and $C_6$-carboxylic acid esters contained in the aqueous phase hydrolyze on repeated recycling of the aqueous phase. The carboxylic acids thus formed form sparingly soluble salts with the cobalt ions and the nitrogen bases, leading to catalyst losses and to clogging of lines. The novel process avoids continuous accumulation of such acids.

In a first stage (stage a) an aqueous cobalt salt solution is treated with carbon monoxide and hydrogen in excess at from 50° to 200° C. and under a pressure of from 50 to 500 bar in the presence of active charcoal charged with cobalt carbonyl. Preferred cobalt salts are water-soluble salts with fatty acids, especially formates, acetates, propionates and butyrates. Cobalt formate and cobalt acetate have proved particularly suitable. It is advantageous to start with solutions which contain from 0.5 to 5% by weight of cobalt, calculated as metal, especially from 1 to 3% by weight of cobalt, in the form of the above salts. In general, the above gas mixture contains carbon monoxide and hydrogen in a volume ratio of from 4:1 to 1:2, especially from 2:1 to 1:1. An about equimolecular mixture of carbon monoxide and hydrogen has proved particularly suitable. Advantageously, the mixture of carbon monoxide and hydrogen is used in excess, for example in up to 5 times the stoichiometrically required amount. The reaction is advantageously carried out at from 100° to 170° C. under a pressure of from 100 to 400 bar. It has furthermore proved advantageous to use an aqueous cobalt salt solution which contains up to 20% by weight, especially from 3 to 10% by weight, of an inert neutral salt, preferably an alkali metal salt of a non-oxidizing acid, e.g., an alkali metal sulfate or alkali metal phosphate.

The treatment in stage a is carried out in the presence of active charcoal. Examples of suitable types of active charcoal are peat charcoal, animal charcoal and sugar charcoal. The first-mentioned has proved particularly suitable. Advantageously, the active charcoal is charged to saturation with cobalt carbonyl. In general, this is achieved by passing an aqueous solution of a cobalt salt, together with the above gas mixture of carbon monoxide and hydrogen, over the active charcoal, under the stated reaction conditions, until the charcoal is saturated, ie. until cobalt carbonyl or cobalt carbonyl hydride is analytically detectable in the material which leaves the reactor.

In general, the treatment is carried out in a treatment zone in which the length:diameter ratio is advantageously from 5:1 to 50:1, and in which the active charcoal is as a rule arranged as a fixed bed. Preferably, a throughput of from 1.5 to 15 g/hour of cobalt, calculated as metal but used in the form of the above salts, is maintained per kilogram of active charcoal.

The resulting aqueous solution, containing cobalt carbonyl hydride, unconverted cobalt salts and liberated acid, is fed, advantageously together with the unconsumed mixture of carbon monoxide and hydrogen, and advantageously without reduction of pressure, to the second stage (stage b). There, the cobalt carbonyl hydride is extracted with butadiene or a butadiene-containing hydrocarbon mixture, which will be discussed in more detail later. Either the entire amount of butadiene required for the carbonylation, or only a part thereof, may be used for the extraction. Advantageously, from 5 to 30 moles of butadiene are used per gram atom of cobalt to be extracted. The extraction is carried out in counter-current or in co-current in equipment conventionally used for industrial extractions, for example in columns or static mixers. During their extraction, the temperature is maintained at from 20° to 100° C. and the pressure at from 5 to 300 bar. The mixture is subsequently separated into an aqueous phase and an organic phase. If, for example, the extraction is carried out in a pressure tube filled with Raschig rings, separation into an organic phase and an aqueous phase takes place simultaneously, in the upper part of the tube. At the same time, the mixture of carbon monoxide and hydrogen is removed as the gas phase. The cobalt content of the organic phase leaving stage b is in general from 1 to 5% by weight. We assume that the cobalt carbonyl is present in the organic phase as a water-insoluble complex with butadiene.

In stage c, the organic phase is then reacted with an excess of an alkanol of 1 to 4 carbon atoms, at from 80° to 150° C. and under a pressure of from 300 to 2,000 bar, in the presence of from 0.5 to 2 moles of a tertiary nitrogen base, having a $pK_a$ of from 3 to 11, per mole of butadiene, with the proviso that the tertiary nitrogen base should preferably be lower-boiling than the pentenoic acid ester to be produced.

If less than the entire amount of butadiene or butadiene-containing hydrocarbon mixture required for the carbonylation was employed for the extractions, the required additional amount of starting material is added in stage (c). It may be noted that instead of pure butadiene, a butadiene-containing hydrocarbon mixture may be used advantageously. Such hydrocarbon mixtures contain, in addition to butadiene, saturated hydrocarbons of 3 to 5 carbon atoms and olefinically monounsaturated olefins of 3 to 5 carbon atoms. The butadiene content should as a rule be greater than 10% by weight. In particular, $C_4$-cuts are used as the starting mixture in industrial operation. For the purposes of the invention, the term $C_1$–$C_4$-cut is applied to any mixture of predominantly non-branched $C_4$-hydrocarbons which contains more than 10% by weight of 1,3-butadiene (butadiene) and more than 15% of butenes. Depending on the origin of the cut, the individual components in such mixtures are normally present in the following proportions:

Butadiene: from 10 to 70, on average from 40 to 60, % by weight

Isobutene: from 15 to 40, on average from 20 to 35, % by weight

But-1-ene: from 10 to 40, on average from 10 to 25, % by weight

But-2-ene: from 5 to 20, on average from 5 to 15, % by weight

Butanes: from 1 to 10, on average from 1 to 10, % by weight

Butynes: from 0.1 to 3, on average from 0.1 to 3, % by weight

Such $C_4$-cuts are obtained, for example, on dehydrogenating butane or butene, or as by-products from the production of ethylene by thermal cracking of naphtha or of higher hydrocarbon cuts.

Preferred tertiary nitrogen bases are N-heterocyclic compounds, e.g., pyridine ($pK_a$ 5.3), methylpyridines, e.g., 3-picoline ($pK_a$ 6.0) and isoquinoline ($pK_a$ 5.4), as well as trialkylamines, e.g., trimethylamine ($pK_a$ 9.8) or triethylamine ($pK_a$ 11.0). Pyridine is of particular industrial importance.

It has proved particularly advantageous to use from 0.6 to 1.5 moles of tertiary nitrogen base per mole of butadiene.

Preferably, a tertiary nitrogen base which is lower-boiling than the particular pentenoic acid ester produced is employed.

Examples of suitable alkanols of 1 to 4 carbon atoms are methanol, ethanol, propanol, butanol and isobutanol. The use of methanol is particularly preferred.

The reaction is advantageously carried out at from 120° to 140° C. under a pressure of from 600 to 1,200 bar. As a rule, from 0.01 to 0.1 gram atom of cobalt, in the form of the cobalt carbonyl complexes described, is employed per mole of butadiene.

In this context, it is noteworthy that when using $C_4$-cuts the butenes additionally present do not react, to give the corresponding carboxylic acid esters, under the specified reaction conditions, though such reaction would have been expected from German Laid-Open Application DOS No. 2,023,690.

In addition to unconverted butadiene, the reaction mixture obtained may or may not contain other hydrocarbons, tertiary nitrogen bases, cobalt carbonyl, unconverted alkanols, and the pentenoic acid esters formed as useful products, as well as by-products, e.g., valeric acid esters, vinylcyclohexene, butenyl ketones and butyl ketones, and butadiene polymers.

After releasing the pressure, the tertiary nitrogen bases contained in the above reaction mixture are removed from the latter to the extent of leaving from 0.1 to 0.3 mole per mole of pentenoic acid ester, and any excess hydrocarbons are also removed (stage d). This removal may be effected by distillation or by other separation processes, e.g., extraction. Advantageously, the tertiary nitrogen bases and any excess hydrocarbons are removed by distillation under reduced pressure.

In carrying out the distillation, the temperature in the distillation residue should not exceed 75° C., to avoid decomposing the cobalt catalyst. Depending on the choice of the alkanol present, some or all of the excess alkanol distils off at the same time.

The penetenoic acid ester remaining in the reaction mixture is reacted with carbon monoxide and an excess of an alkanol of 1 to 4 carbon atoms, if necessary after having again added an appropriate amount of alkanol, at from 140 to 200° C. and under a pressure of from 100 to 400 bars, in the presence of the amount of cobalt catalyst and tertiary nitrogen base contained in the reaction mixture. Advantageously, this reaction is carried out at from 150° to 180° C. Preferably, the amount of alkanol present is from 1.5 to 4 moles per mole of pentenoic acid ester. Further, it has proved advantageous to add to the carbon monoxide a few percent by volume of hydrogen, e.g., from 1 to 4 percent by volume, in order to increase the rate of reaction. After releasing the pressure, the excess alkanol, and the free tertiary nitrogen base, are distilled from the reaction mixture obtained. The chemically bonded tertiary nitrogen base (from 1 to 2 moles per gram atom of cobalt) is not distilled off at the same time. To avoid decomposition of the cobalt complex, accompanied by undesirable formation of cobalt metal, it has proved advantageous to pass a slow stream of carbon monoxide, or of a gas containing carbon monoxide, into the bottom of the column.

The remaining reaction mixture, containing catalyst, butanedicarboxylic acid ester and by-products, is treated, in stage (e), with an oxidizing agent in an aqueous acid medium. Suitable oxidizing agents are especially those which do not contaminate the reaction mixture, for example hydrogen peroxide, oxygen or an oxygen-containing gas. The use of a gas containing molecular oxygen, in particular air, is particularly preferred. The oxidizing agent is used in an amount corresponding to at least two oxidation equivalents per mole of cobalt compound, but is preferably employed in excess. In practice it has proved advantageous to use from 30 to 300 liters (S.T.P.) of air per kg of reaction mixture.

In general, from 0.1 to 10 parts by weight, advantageously from 0.2 to 1 part by weight, of water is used per part by weight of the reaction mixture. The pH is advantageously from 3 to 6. Suitable acids are non-oxidizing mineral acids and fatty acids. The aqueous acid solution obtained in stage b after removing the butadiene containing cobalt carbonyl hydride is particularly suitable. For example, if cobalt acetate is used as a starting material, such a solution contains acetic acid in addition to unreacted cobalt acetate. If necessary, a suitable fatty acid may be introduced additionally. It is necessary to ensure, under all circumstances, that there is sufficient acid present to keep the cobalt salt in solution. The same is true of the amount of water to be used. In order that the cobalt solution obtained should not be excessively dilute, it is advantageous to recycle the aqueous cobalt-containing solution to the treatment chamber and only to separate off a small branch-stream, corresponding to the amount added.

The treatment is advantageously carried out at from 80° to 160° C., more especially at from 100° to 130° C. Depending on the degree of mixing, the reaction may be complete after only a few seconds and in many cases after only a fraction of a second. To ensure thorough mixing it is advantageous to introduce the reaction mixture in fine dispersion into the aqueous acid solution, whilst at the same time introducing the oxidizing agent, e.g., air.

After the treatment, the liquid phase is separated, for example by decanting, into an organic phase and an aqueous phase. To facilitate phase separation, it has proved advantageous if the aqueous acid medium contains an inert neutral salt, for example, an alkali metal salt of a non-oxidizing acid, e.g., sodium sulfate. It is also advantageous to add up to 20% by weight of hydrocarbons to the organic phase. The excess hydrocarbons distilled off in stage (d), after the first carbonylation, are particularly suitable for this purpose.

According to the invention, the aqueous phase, containing cobalt salt, obtained from stage (e) is extracted with water-immiscible solvents.

Suitable extractants are all solvents which are inert under the extraction conditions and are immiscible with water. The use of hydrocarbons, e.g., hexane, cyclohexane, pentane or a $C_4$-cut (a mixture of butane and butenes) as well as of ketones, e.g., dibutyl ketone, diisopropyl ketone or methyl isobutyl ketone, is preferred. Other suitable solvents are ethers, e.g., diethyl ether, diisopropyl ether and methyl isobutyl ether. The use of hydrocarbon extractants is particularly preferred.

The extraction can be carried out in all suitable industrially used equipment. Examples of suitable equipment include pulsation columns, static mixers and apparatus operating on the mixer settler principle. The extraction is advantageously carried out in counter-current, as a rule at the temperature at which the aqueous phase is obtained after removing the organic phase, for example at from 40° to 80° C.

After separating off the organic phase, the aqueous phase containing cobalt salts is reused to prepare the catalyst solution, for example in stage (a). It has also proved advantageous to feed the organic phase obtained to the reaction mixture after the oxidative treatment in an aqueous acid medium according to stage (e). This achieves better separation into an organic phase and an aqueous phase. Thereafter, the organic solvent is recovered by distillation when isolating the butanedicarboxylic acid ester and is reused for extracting the aqueous phase.

As a rule, from 0.5 to 2 parts of solvent are used per part by volume of aqueous solution containing cobalt salts.

Furthermore, it has proved advantageous to treat the recycled aqueous solution containing cobalt salts with a strongly basic ion exchanger, preferably in the form of the acetate. Examples of suitable ion exchangers are those based on crosslinked polystyrenes and containing quaternary ammonium groups. The fourth ligand on the N atom is preferably a methyl, hydroxyethyl or benzyl radical. The capacity of the ion exchanger is in general from 0.5 to 3 equivalents/liter.

An example of such an ion exchanger is Amberlite ® IRA 400 from Rohm and Haas, Philadelphia.

The treatment with ion exchangers may be carried out, for example, after the extraction of the aqueous phase containing cobalt carbonyl hydride. Accordingly, the treatment is advantageously carried out on the aqueous phase separated off in stage b, before this phase is recycled to stage (e). It is possible to treat the entire aqueous phase periodically, for example when the content of adipic acid has reached 1.5 percent by weight, or to treat a part-stream continuously.

Fractional distillation of the organic phase yields residual pyridine, unconverted pentenoic acid ester, which are recycled to the carbonylation reaction, and a mixture of butanedicarboxylic acid esters (from 80 to 85% by weight of adipic acid esters, from 11 to 15% by weight of 2-methyl-glutaric acid esters and from 3 to 6% by weight of 2-ethylsuccinic acid esters). The ester mixture may be used for the manufacture of diols or polyesters. The adipic acid ester obtainable from the ester mixture by fractional distillation may be used to manufacture adipic acid, AH salt, adipodinitrile and 1,6-hexanediol.

The aqueous phase containing cobalt salts is advantageously recycled to stage (a), as the starting solution for the preparation of cobalt carbonyl hydride. The process of the invention is outstandingly suitable for continuous industrial operation.

Butanedicarboxylic acid esters may be used for the manufacture of polymers.

The Examples which follow illustrate the process of the invention.

EXAMPLE

A high pressure tube filled with 600 ml of active charcoal (from Norit, particle size from 3 to 5 mm) is charged with 180 ml/hour of an aqueous cobalt acetate solution containing 2.5 percent by weight of cobalt$^{2+}$. This solution is obtained as the aqueous phase in stage (e). In addition, 50 liters (S.T.P.) per hour of an equimolar mixture of carbon monoxide and hydrogen are introduced, whilst maintaining a temperature of 120° C. and a pressure of 300 bar. The solution taken off the lower part of the tube contains 0.65 percent by weight of cobalt$^{2+}$ and 1.85 percent by weight of cobalt in the form of cobalt carbonyl hydride, as well as the corresponding amount of acetic acid. After letting down to 20 bar the solution is thoroughly mixed, at room temperature, with 310 ml of a C$_4$-cut which contains 43 percent by weight of butadiene (1.57 moles). After phase separation, the C$_4$-cut contains 3.7 g of cobalt in the form of cobalt carbonyl compounds. This cobalt-containing C$_4$-cut is now fed to a high pressure vessel of 1.9 liters capacity, into which there are also introduced, per hour, 127 ml (1.57 moles) of pyridine, 127 ml (3.14 moles) of methanol and 60 liters (S.T.P.) of carbon monoxide. The carbonylation takes place at 130° C. and 600 bar. The product taken off at the top of the high pressure vessel is let down, in the course of which excess C$_4$ hydrocarbons are separated off as a gas, in addition to excess carbon monoxide. These hydrocarbons contain virtually no butadiene. Per hour, about 52 g of methanol and 100 g of pyridine are distilled from the discharged material, the distillation being carried out under reduced pressure in order not to damage the catalyst. The maximum temperature in the distillation residue is 65° C. This residue, which contains 3.7 g of cobalt as a carbonyl complex and 165 g (1.44 moles) of pentenoic acid ester, is fed, together with 117 ml (2.88 moles) of methanol and 55 liters (S.T.P.) of carbon monoxide containing 2 percent by volume of hydrogen, continuously into the bottom of a further high pressure vessel of 1.7 liters capacity. The carbonylation is carried out at 170° C. and under a pressure of 150 bar. The excess methanol, and the free pyridine, are distilled from the discharged material in a further column, whilst introducing about 50 liters (S.T.P.) of carbon monoxide per hour. The distillation residue (265 g per hour) is thoroughly mixed with 200 ml per hour of the aqueous acetic acid solution obtained from extraction stage (b), in a tube filled with Raschig rings, whilst passing about 50 liters (S.T.P.) of air through the mixture at 100° C.

After the phase separation, 200 ml of aqueous cobalt acetate solution are obtained, from which small amounts of pyridine are distilled off. The organic phase is worked up by fractional distillation. The aqueous phase obtained is extracted with an equal part by volume of cyclohexane in a countercurrent pulsation column, 1.5 mm long and 30 mm in diameter, which is filled with Raschig rings. The organic phase is introduced into stage (e) before the phase separation. After the extraction, no dimethyl adipate, and only traces of monomethyl adipate, are detectable in the aqueous phase. The aqueous solution is recycled to stage a as the starting solution for the formation of the catalyst. After 25 cycles of the aqueous phase, no precipitation of sparingly soluble cobalt salts was as yet observed. In continuing the process, the aqueous phase is additionally treated —after the extraction—with a strongly basic ion exchanger (Amberlite ®IRA 400 from Rohm and Haas, Philadelphia) in the acetate form. No residual free adipic acid is detectable in the aqueous solution.

COMPARATIVE EXAMPLE

The procedure described in Example 1 is followed, without extracting the aqueous solution or treating it with ion exchangers. 1.5 percent by weight of dimethyl adipate remain in the aqueous phase from stage (e). After 5 cycles of the aqueous phase, the content of monomethyl adipate has built up to 1.3%, and the content of adipic acid to 1.5%, due to hydrolysis of the entrained esters. On continuing the reaction, cobalt pyridine adipates precipitate from the aqueous phase, causing catalyst losses.

We claim:

1. In a process for the manufacture of butanedicarboxylic acid esters, by reacting butadiene or a hydrocarbon mixture containing butadiene with carbon monoxide and an alkanol of 1 to 4 carbon atoms in the presence of a tertiary nitrogen base and a cobalt carbonyl compound at from 80° to 150° C. under superatmospheric pressure and then, without removing the catalyst, reacting the pentenoic acid ester obtained further with carbon monoxide and an alkanol of 1 to 4 carbon atoms at from 140° to 200° C. under superatmospheric pressure, to give a butanedicarboxylic acid ester, wherein
   (a) an aqueous cobalt salt solution is treated, at from 50° to 200° C. under pressures of from 50 to 500 bar, with excess carbon monoxide and hydrogen in the presence of active charcoal charged with cobalt carbonyl,
   (b) the resulting aqueous solution of cobalt carbonyl hydride is extracted with butadiene or a hydrocarbon mixture containing butadiene and the aqueous phase is separated off,
   (c) the butadiene, or butadiene-containing hydrocarbon mixture, which contains cobalt carbonyl hydride, cobalt carbonyl and butenyl-cobalt tricarbonyl is reacted with carbon monoxide and an excess of an alkanol of 1 to 4 carbon atoms in the presence of from 0.5 to 2 moles, per mole of butadiene, of a tertiary nitrogen base having a $pK_a$ of from 3 to 11, at from 80° to 150° C., under a pressure of from 300 to 2,000 bar, (d) the tertiary nitrogen bases contained in the reaction mixtures thus obtained are removed to the extent of leaving from 0.01 to 0.3 mole per mole of pentenoic acid ester produced, excess hydrocarbon is also removed, the pentenoic acid ester remaining in the reaction mixture is reacted with carbon monoxide and an excess of an alkanol of 1 to 4 carbon atoms at from 140° to 200° C. under a pressure of from 100 to 400 bar in the presence of the amount of cobalt carbonyl and tertiary nitrogen base remaining in the reaction mixture and thereafter the excess alkanol and free tertiary nitrogen base are distilled off, and (e) the residual reaction mixture, containing cobalt catalyst, butanedicarboxylic acids and by-products, is treated with an oxidizing agent in an aqueous acid medium and the mixture is separated into an organic phase, from which butanedicarboxylic acid ester is isolated by distillation, and an aqueous phase containing cobalt salts, the improvement wherein the aqueous phase containing cobalt salts is extracted with a water-immiscible solvent.

2. A process as claimed in claim 1, wherein the aqueous phase, after the extraction, is additionally treated with a strongly basic ion exchanger.

3. A process as claimed in claim 1, wherein the solvent separated off as the organic phase after the extraction is added to the organic phase in stage (e) after treatment with an oxidizing agent in an aqueous acid medium.

* * * * *